United States Patent
Jimenez, Jr. et al.

(10) Patent No.: US 10,261,033 B2
(45) Date of Patent: Apr. 16, 2019

(54) MATERIAL IDENTIFICATION SYSTEM

(71) Applicant: National Technology & Engineering Solutions of Sandia, LLC, Albuquerque, NM (US)

(72) Inventors: Edward Steven Jimenez, Jr., Albuquerque, NM (US); Kyle R. Thompson, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 528 days.

(21) Appl. No.: 14/601,103

(22) Filed: Jan. 20, 2015

(65) Prior Publication Data
US 2016/0209335 A1   Jul. 21, 2016

(51) Int. Cl.
*G01N 23/04* (2018.01)
*G01V 5/00* (2006.01)

(52) U.S. Cl.
CPC .............. *G01N 23/04* (2013.01); *G01V 5/00* (2013.01); *G01V 5/0016* (2013.01)

(58) Field of Classification Search
None
See application file for complete search history.

(56) References Cited

U.S. PATENT DOCUMENTS

| | | | | |
|---|---|---|---|---|
| 7,957,505 B1* | 6/2011 | Katz | ...................... | G01B 15/00 378/147 |
| 2007/0006651 A1* | 1/2007 | Kruger | .................. | G01N 29/11 73/579 |
| 2007/0268997 A1* | 11/2007 | Zhu | ...................... | A61B 6/5282 378/7 |
| 2010/0119103 A1* | 5/2010 | Ewert | .................. | G01B 15/045 382/100 |
| 2011/0243382 A1* | 10/2011 | Morton | .................. | A61B 6/032 382/103 |
| 2014/0270440 A1* | 9/2014 | Inglese | ................ | A61B 6/4241 382/131 |

OTHER PUBLICATIONS

Dimple Modgil, in material identification in x-ray microscopy and micro CT using multi-layer, multi-color scintillation detectors, Oct. 21, 2015, 32 pages.*
Jimenez, Jr., "Simulation and Estimation of Organ Uptake in a Digital Mouse Phantom," Doctoral Dissertation, The University of Arizona, Oct. 2010, 254 pages.

(Continued)

*Primary Examiner* — Tung S Lau
(74) *Attorney, Agent, or Firm* — Yee & Associates, P.C.

(57) ABSTRACT

A method and apparatus for identifying a material in an object. An image of the object generated from energy passing through the object is obtained by a computer system. The computer system estimates attenuations for pixels in a sensor system from the image of the object to form estimated attenuations. The estimated attenuations represent a loss of the energy that occurs from the energy passing through the object. The computer system also identifies the material in the object using the estimated attenuations and known attenuation information for identifying the material in the object.

11 Claims, 8 Drawing Sheets

(56) References Cited

OTHER PUBLICATIONS

Chen, "System Calibration and Image Reconstruction for a New Small-Animal SPECT System," Doctoral Dissertation, The University of Arizona, Sep. 2006, 315 pages.
Park, "Novel Applications Using Maximum-Likelihood Estimation in Optical Metrology and Nuclear Medical Imaging: Point-Diffraction Interferometry and Bazookapet," Doctoral Dissertation, The University of Arizona, Apr. 2014, 186 pages.
Hubbell et al., "Tables of X-Ray Mass Attenuation Coefficients and Mass Energy Absorption Coefficients from 1 keV to 20 MeV for Elements Z=1 to 92 and 48 Additional Subtances of Dosimetric Interest," U.S. Department of Commerce, The National Institute of Standards and Technology, last updated Oct. 2014, 1 page, accessed Jan. 14, 2015. http://www.nist.gov/pml/data/xraycoef/.
Jimenez, et al., "Utilization of Virtualized Environments for Efficient X-ray Attenuation Approximation," ASNT 23rd Research Symposium, Mar. 2014, 5 pages.
Jimenez, et al., "Exploring Mediated Reality to Approximate X-ray Attenuation Coefficients from Radiographs," SPIE vol. 9215, Radiation Detectors: Systems and Applications XV, Sep. 2014, 11 pages.

\* cited by examiner

MATERIAL IDENTIFICATION SYSTEM

GOVERNMENT LICENSE RIGHTS

This invention was made with United States Government support under Contract No. DE-AC04-94AL85000 between Sandia Corporation and the United States Department of Energy. The United States Government has certain rights in this invention.

BACKGROUND INFORMATION

1. Field

The present disclosure relates generally to an improved object scanning system and, in particular, to a method and apparatus for identifying a material in an object using an object scanning system. Still more particularly, the present disclosure relates to a method and apparatus for identifying a material in an object from estimating the attenuation of x-rays passing through the object.

2. Background

X-ray scanners are used for a variety of purposes. For example, x-ray scanners may be used for medical purposes. X-ray scanners may be used to visualize bone structures, dense tissues, and for other medical purposes. As another example, x-ray scanners are also used for security purposes to scan luggage, baggage, and other containers that may be placed onto commercial vehicles or brought into buildings or other areas. X-ray scanners also may be used for industrial purposes to inspect objects.

With x-ray scanners, images may be generated in which internal structures or other objects within an object of interest may be detected. In an x-ray scanner, a source emits x-rays that pass through an object to a detector. Some of the x-rays may be absorbed, or absorbed and scattered. An image may be generated from the x-rays detected by the detector.

In some cases, it is desirable to identify the material in an object. For example, in scanning luggage, it may be desirable to know whether an object is made of metal, plastic, or some other type of material. Additionally, it may be desirable to know the type of metal or plastic in the object. Currently used x-ray scanners, however, do not provide an identification of the material that may form an object with a desired level of accuracy, or as quickly as desired.

Therefore, it would be desirable to have a method and apparatus that takes into account at least some of the issues discussed above, as well as other possible issues. For example, it would be desirable to have a method and apparatus that identifies the material in an object more quickly and accurately than with currently available x-ray scanning systems.

SUMMARY

An illustrative embodiment of the present disclosure provides a method for identifying a material in an object. An image of the object generated from energy passing through the object is obtained by a computer system. The computer system estimates attenuations for pixels in a sensor system from the image of the object to form estimated attenuations. The estimated attenuations represent a loss of the energy that occurs from the energy passing through the object. The computer system also identifies the material in the object using the estimated attenuations and known attenuation information for identifying the material in the object.

Another illustrative embodiment of the present disclosure provides an object identification system. The object identification system comprises an object analyzer that obtains an image of an object generated from energy passing through the object and estimates attenuations for pixels in a sensor system from the image of the object to form estimated attenuations. The attenuations represent an energy loss that occurs from the energy passing through the object. The object analyzer also identifies a material in the object using the estimated attenuations and known attenuation information for identifying the material in the object.

Yet another illustrative embodiment of the present disclosure provides a computer program product for identifying a material in an object. The computer program product comprises a computer readable storage media, first program code, second program code, and third program code. The first program code is stored on the computer readable storage media and obtains an image of the object generated from energy passing through the object. The second program code is stored on the computer readable storage media and estimates, by the computer system, attenuations for pixels in a sensor system from the image of the object to form estimated attenuations. The attenuations represent a loss of the energy that occurs from the energy passing through the object. The third program code is stored on the computer readable storage media and identifies, by the computer system, the material in the object using the estimated attenuations and known attenuation information for identifying the material in the object.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account one or more different considerations. For example, the illustrative embodiments recognize and take into account that currently available x-ray scanners do not provide an ability to identify a material of an object. The illustrative embodiments recognize and take into account that one manner in which the material may be identified in an object is through measuring the attenuation of the x-rays passing through the object. The illustrative embodiments recognize and take into account that in measuring attenuation, energy in the form of mono-energetic x-rays is needed to accurately measure the attenuation of x-rays passing through an object. The illustrative embodiments recognize and take into account that currently available x-ray scanners generate poly-energetic x-ray beams. For example, the x-rays may have a distribution of energies rather than a single energy.

The illustrative embodiments recognize and take into account that measuring attenuation in poly-energetic x-rays may be more time-consuming and difficult than desired. Thus, the illustrative embodiments recognize and take into account that estimating the attenuation may be performed to identify materials in objects. These embodiments provide a method and apparatus for identifying a material in an object.

Figure 1:
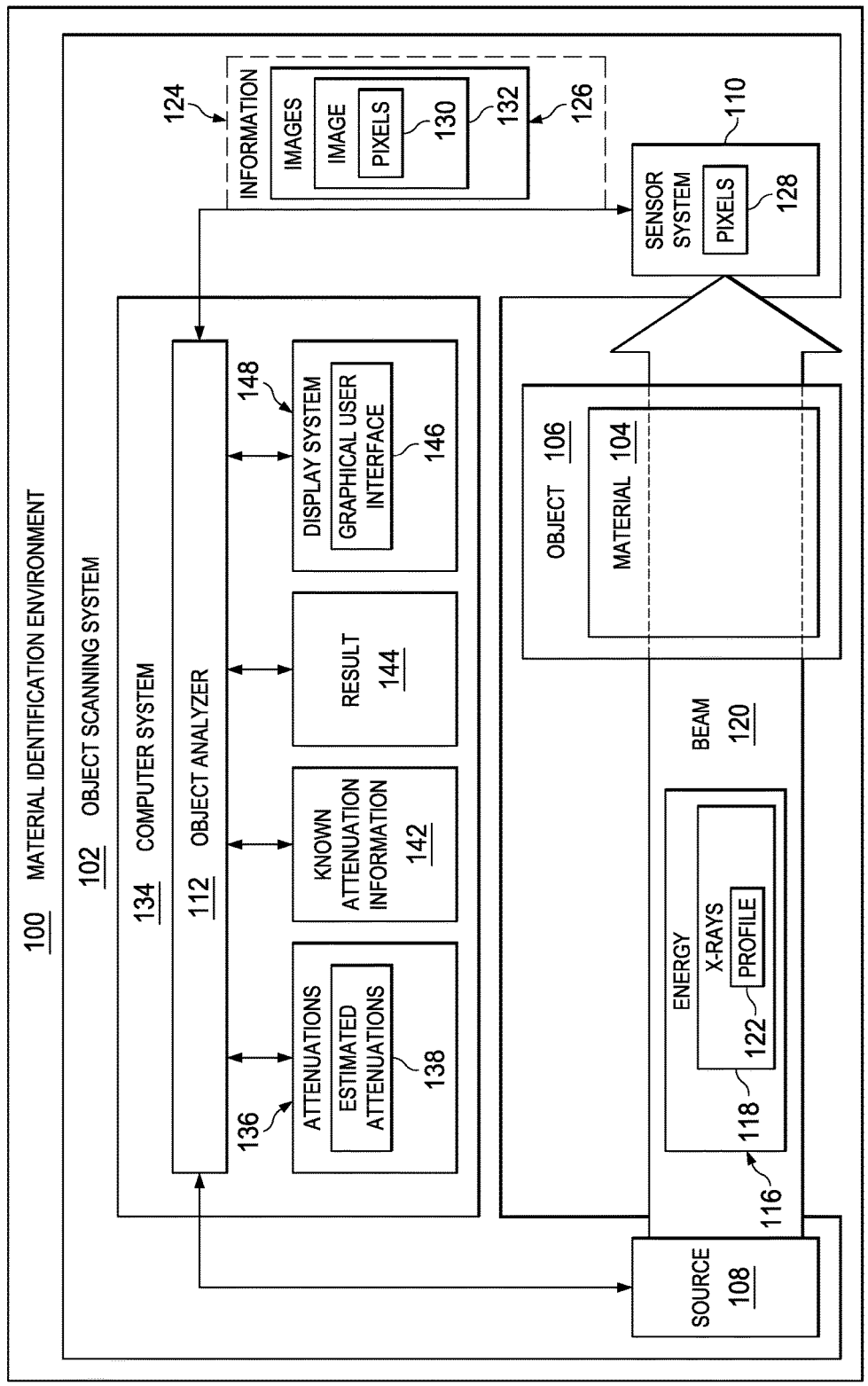
FIG. 1 is an illustration of a block diagram of a material identification environment in accordance with an illustrative embodiment.

With reference now to the figures, and in particular with reference to FIG. 1, an illustration of a block diagram of a material identification environment is depicted in accordance with an illustrative embodiment. In this illustrative example, material identification environment 100 is an environment in which object scanning system 102 identifies material 104 in object 106.

In this illustrative example, material 104 may be part of object 106 or may be contained within object 106. Material 104 may be, for example, a solid, a liquid, or a gas. In this illustrative example, object scanning system 102 may provide different levels of granularity in identifying material 104. For example, object scanning system 102 may identify material 104 as a liquid, a plastic, or a metal. In another illustrative example, object scanning system 102 may be able to identify material 104 with more specificity. For example, object scanning system 102 may identify material 104 as a type of metal such as aluminum, iron, steel, copper, nickel, titanium, or some other suitable type of metal.

Object scanning system 102 may take various forms. In this illustrative example, scanning of an object is performed with at least one of an x-ray scanner, a positron emission tomography (PET) scanner, a single photon emission computer tomography scanner (SPECT) scanner, or some other suitable device.

As used herein, the phrase "at least one of," when used with a list of items, means different combinations of one or more of the listed items may be used and only one of each item in the list may be needed. In other words, at least one of means any combination of items and number of items may be used from the list but not all of the items in the list are required. The item may be a particular object, thing, or a category.

For example, without limitation, "at least one of item A, item B, or item C" may include item A, item A and item B, or item B. This example also may include item A, item B, and item C or item B and item C. Of course, any combinations of these items may be present. In some illustrative examples, "at least one of" may be, for example, without limitation, two of item A; one of item B; and ten of item C; four of item B and seven of item C; or other suitable combinations.

In the illustrative example, object scanning system 102 includes a number of different components. As depicted, object scanning system 102 is comprised of source 108, sensor system 110, and object analyzer 112.

As depicted, source 108 emits energy 116. For example, when object scanning system 102 is an x-ray scanner, source 108 emits energy 116 in the form of x-rays 118. X-rays 118 may be emitted from source 108 in the form of beam 120.

In this illustrative example, x-rays 118 has profile 122. Rays in x-rays 118 have different levels of energy 116. In particular, x-rays 118 are poly-energetic x-rays in this illustrative example. For example, if x-rays 118 is selected to be emitted at 160 KeV, x-rays 118 may have levels of energy 116 that are up to 160 KeV. The distribution of the different levels of energy 116 form profile 122.

As depicted, energy in the form of beam 120 of x-rays 118 is directed to pass through object 106 to reach sensor system 110. In this illustrative example, sensor system 110 generates information 124 from energy 116 reaching sensor system 110. As depicted, information 124 includes images 126. Images 126 may be generated from a single emission of energy 116 or sequential emissions of energy 116 that are detected by sensor system 110 in this particular example.

In this illustrative example, sensor system 110 is hardware. As depicted, sensor system 110 includes pixels 128. Pixels 128 are elements in sensor system 110 that detect energy 116 reaching pixels 128 from source 108 that passed through object 106. These pixels may form one or more sensors in sensor system 110. In these illustrative examples, these pixels detect x-rays 118. Pixels 128 correspond to pixels 130 in image 132 in images 126 using energy 116 detected by sensor system 110. Sensor system 110 also may include other components, such as processors, filters, or other suitable components for generating information 124.

As depicted, sensor system 110 may be a single channel sensor or a multi-channel sensor. When sensor system 110 is a single channel sensor, image 132 is generated when energy 116 is detected by sensor system 110. When sensor system 110 is a multi-channel sensor, images 126 are generated when energy 116 is detected by sensor system 110. Each channel in a multi-channel sensor, may receive different ranges of energy levels in energy 116 detected by sensor system 110.

In this illustrative example, object analyzer 112 identifies material 104 in object 106. Object analyzer 112 identifies material 104 from one or more of images 126.

As depicted, object analyzer 112 may be implemented in software, hardware, firmware or a combination thereof. When software is used, the operations performed by object analyzer 112 may be implemented in program code configured to run on hardware, such as a processor unit. When firmware is used, the operations performed by object analyzer 112 may be implemented in program code and data and stored in persistent memory to run on a processor unit. When hardware is employed, the hardware may include circuits that operate to perform the operations in object analyzer 112.

In the illustrative examples, the hardware may take the form of a circuit system, an integrated circuit, an application specific integrated circuit (ASIC), a programmable logic device, or some other suitable type of hardware configured to perform a number of operations. With a programmable logic device, the device may be configured to perform the number of operations. The device may be reconfigured at a later time or may be permanently configured to perform the number of operations. Programmable logic devices include, for example, a programmable logic array, a programmable array logic, a field programmable logic array, a field programmable gate array, and other suitable hardware devices. Additionally, the processes may be implemented in organic components integrated with inorganic components and may be comprised entirely of organic components excluding a human being. For example, the processes may be implemented as circuits in organic semiconductors.

As depicted, object analyzer 112 may be in computer system 134. Computer system 134 is a hardware system and includes one or more data processing systems. When more than one data processing system is present, those data processing systems may be in communication with each other using a communications medium. The communications medium may be a network. The data processing systems may be selected from at least one of a computer, a server computer, a tablet, or some other suitable data processing system.

During operation, object analyzer 112 may control source 108 to send energy 116 through object 106 to sensor system 110. Object analyzer 112 obtains image 132 of object 106 generated from energy 116 passing through object 106. Image 132 may be part of information 124 sent by sensor system 110 to object analyzer 112. Information 124 also may include information about parameters, settings, or other information that may be generated by sensor system 110.

Object analyzer 112 estimates attenuations 136 for pixels 128 in sensor system 110 from image 132 of object 106 to form estimated attenuations 138. In the illustrative example, estimated attenuations 138 represent a loss of energy 116 that occurs from energy 116 passing through object 106. With energy in the form of x-rays, the loss of energy 116 may be from at least one of photons in energy 116 that do not reach sensor system 110, or photons that are detected by sensor system 110 but with an energy level that is lower than when the photons were emitted from source 108. The lower energy level may be a loss in intensity in energy 116.

In the illustrative example, object analyzer 112 identifies material 104 in object 106 using estimated attenuations 138 and known attenuation information 142 for identifying material 104 in object 106. The estimation may be performed in a number of different ways. For example, estimates of attenuations 136 may be performed by finding an average attenuation for image 132 or by solving a system of equations for images 126 at the same time. The system of equations may be selected from one of a system of linear equations, a system of non-linear equations, a pseudo-inverse, a matrix inversion, or other suitable types of systems of equations.

For example, estimated attenuations 138 may be estimated for each of pixels 128 in sensor system 110. Next, an average attenuation may be calculated from estimated attenuations 138 to form an estimated attenuation for image 132. This process may be performed for each of images 126 generated by sensor system 110. As depicted this process is a direct search for estimated attenuations 138.

In another illustrative example, images 126 may be generated from a single transmission of energy 116 from source 108 when sensor system 110 is a multi-channel sensor. Pixels 130 in images 126 may be used to fit a system of equations to generate a curve of the attenuation in which each point on the curve represents attenuation for an image in images 126. This process is an iterative process for solving a system of equations using an equation solver to obtain an attenuation profile. The attenuation profile estimates attenuations 136 for images 126 generated from a transmission of energy 116 to a multi-channel sensor.

The identification of material 104 in object 106 forms result 144. Result 144 also may include instructions on how to handle object 106, warnings, confirmations, and other suitable information regarding the identification of material 104. As depicted, result 144 may be displayed in graphical user interface 146 in display system 148 in computer system 134.

Display system 148 is a hardware system and includes one or more display devices on which graphical user interface 146 may be displayed. The display devices may include at least one of a light emitting diode display (LED), a liquid crystal display (LCD), an organic light emitting diode display (OLED), or some other suitable device on which graphical user interface 146 can be displayed.

Result 144 may take different forms. For example, result 144 may include image 132 with an identification of material 104. In particular, image 132 with the identification may be an augmented reality display in graphical user interface 146. In another illustrative example, result 144 may identify an action to be taken.

In the illustrative example, computer system 134 performs a transformation of data. For example, object analyzer 112 receives information 124 with one or more images 126 from sensor system 110 and calculates estimated attenuations 138 for at least one of image 132 in images 126. Estimated attenuations 138 are then used to identify material 104 in object 106.

In an illustrative example image 130 in images 126 and an additional group of images in images 126 may be processed. For example, attenuations for pixels 130 from image 132 and an additional group of attenuations for pixels 130 in sensor system 110 from an additional group of images 126 of object 106 form estimated attenuations and additional estimated attenuations in estimated attenuations 138.

With the identification of object 106, one or more actions may be performed with respect to object 106. An action may be selected from, for example, one of a further inspection of object 106, discarding object 106, indicating object 106 is a permitted object, indicating object 106 is a prohibited object, reworking object 106, sending object 106 to a customer, sending a report to identify material 104 in object 106, displaying an identification of material 104 on image 132 of object 106 as an augmented reality display on display system 148 in computer system 134, or other suitable actions.

Computer system 134 is a special purpose computer system in this illustrative example. With object analyzer 112, computer system 134 identifies material 104 in object 106 with a level of specificity more quickly than with currently used computer systems. Object analyzer 112 identifies material 104 with different levels of specificity. For example, in addition to determining whether material 104 is a plastic, object analyzer 112 may also identify the type of plastic. For example, object analyzer 112 may determine whether the plastic is a polycarbonate, a polystyrene, a polyvinyl chloride, or some other type of plastic material.

This type of modification may be especially useful for identifying materials in situations in which high volumes of objects are to be analyzed quickly. For example, object analyzer 112 may be used in baggage scanning, part inspections, and other suitable uses.

Figure 2:
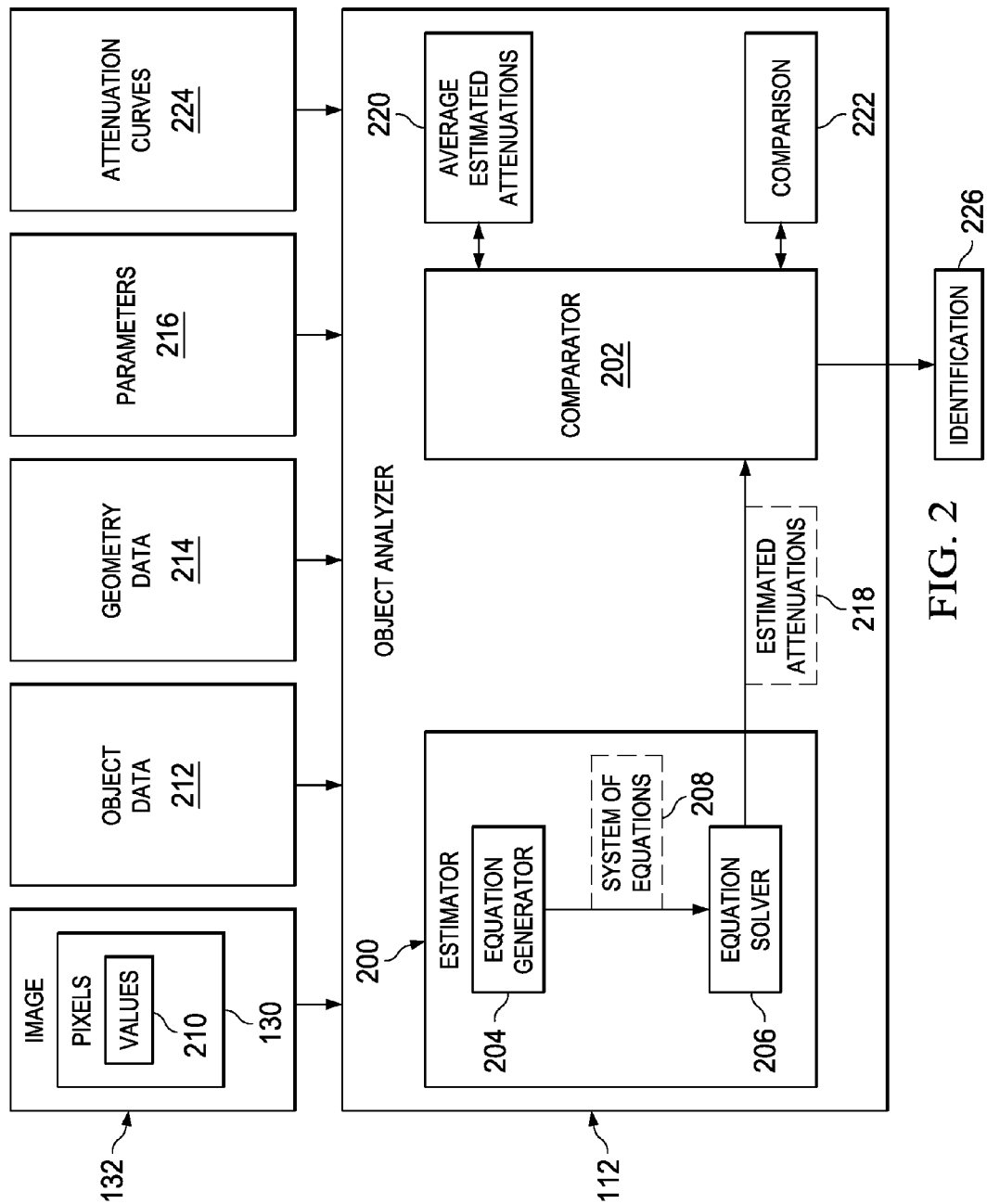
FIG. 2 is an illustration of a block diagram of an information flow for identifying material in an object in accordance with an illustrative embodiment.

Turning now to FIG. 2, an illustration of a block diagram of an information flow for identifying a material in an object is depicted in accordance with an illustrative embodiment. The information flow depicted in FIG. 2 is implemented by object analyzer 112. In the illustrative examples, the same reference numeral may be used in more than one figure. This reuse of a reference numeral in different figures represents the same element in the different figures.

In this illustrative example, object analyzer 112 includes estimator 200 and comparator 202. As depicted, estimator 200 includes equation generator 204 and equation solver 206. Equation generator 204 generates system of equations 208 to solve for attenuation of energy through points on an object. In this illustrative example, the object is located in image 132. In these illustrative examples, system of equations 208 is selected from one of a system of linear equations, a system of non-linear equations, a pseudo-inverse, or a matrix inversion. The estimator 200 may include processes that involve matrix manipulation or direct search methods.

As depicted, equation generator 204 uses values 210 in image 132 to generate system of equations 208. Values 210 are for pixels 130 in image 132 generated from detection of energy 116 by pixels 128 in sensor system 110 in FIG. 1. As depicted, equation generator 204 also uses object data 212, geometry data 214, and parameters 216 to generate system of equations 208.

Equation solver 206 generates estimated attenuations 218 by solving system of equations 208. Estimated attenuations 138 in FIG. 1 are estimated attenuations 218 in this illustrative example. Comparator 202 receives estimated attenuations 218 from equation solver 206.

As depicted, comparator 202 calculates average estimated attenuations 220 from estimated attenuations 218. Comparator 202 generates comparison 222 by comparing average estimated attenuations 220 to attenuation curves 224 for known materials. In this illustrative example, known attenuation information 142 takes the form of a group of attenuation curves 224 for known materials.

As depicted, comparison 222 is based on how closely average estimated attenuations 220 match attenuation curves 224. Comparator 202 generates identification 226 based on comparison 222. In the depicted example, a closest match between average estimated attenuations 220 and attenuation curves 224 is the attenuation curve in attenuation curves 224 that matches average estimated attenuations 220 more closely than all other attenuation curves in attenuation curves 224.

As depicted, identification 226 is an identification of material 104 in object 106 as identified from image 132 of object 106. The identification may identify the material as a particular material. For example, the identification may be that the material is plastic, metal, titanium, aluminum, or some other type of material. The identification also may be that the material is unknown.

Object data 212 includes at least one of an outline of the object in image 132, a model of the object, or other suitable types of information about the object. Object data 212 for the object may also include information about sub-objects.

In this illustrative example, sub-objects of an object are components that form the object. These sub-objects may be comprised of the same or different types of materials. For example, when the object is a water bottle, the sub-objects of the water bottle may be a metal cap and a plastic container.

In this illustrative example, geometry data 214 includes at least one of distance from source 108 of energy 116 to sensor system 110, the position of pixels 128 in sensor system 110, or other suitable types of information for identifying geometry data 214 of source 108 of energy 116 and sensor system 110. Parameters 216 are values for variables in system of equations 208. Parameters 216 include profile data for source 108 of energy 116.

In this illustrative example, the profile data for source 108 is a Bremsstrahlung profile for source 108. A Bremsstrahlung profile is an amount of radiation emitted from charged particles. For example, the radiation emitted by source 108 may be x-rays. The Bremsstrahlung profile for source 108 specifies a distribution of energy 116 emitted from source 108. In this example, the distribution of the Bremsstrahlung profile is non-uniform.

Equation generator 204 uses the following double integral formula to model energy 116 being emitted from source 108:

$$I(j) = \int_{\epsilon \in E} \int_{l_j} I_0(\epsilon) e^{\mu(x,\epsilon)x} dx d\epsilon \qquad (1)$$

where "I(j)" is a number of photons transmitted to pixel j of sensor system 110; "$\epsilon$" is epsilon, and epsilon is the energy value of an x-ray photon; "$I_0(\epsilon)$" is a number of initial photons at epsilon; "e" is an exponential value; "$\mu(x,\epsilon)$" is attenuation with respect to position x and epsilon; and "E" is the energy range of all photons. For example, E may be 0 electron volts to one hundred thousand electron volts. In equation (1) "$\epsilon \in E$" reads for epsilon in the range of all photons, and "$l_j$" is the ray-path from source 108 to pixel j of sensor system 110. The ray-path is a vector having magnitude and direction for a portion of energy 116 from source 108.

In this illustrative example, image 132 shows a two-dimensional attenuation of energy 116. The attenuation of energy 116 in image 132 is unique for the type of material of an object in image 132. More particularly, the identification of energy lost to attenuation through the object is based on integration across $\epsilon$ for the non-uniform distribution of energy 116 emitted from source 108.

Equation generator 204 generates system of equations 208 in the form of:

$$\begin{bmatrix} \vec{p}^t & \vec{0} & \cdots & \cdots & \vec{0} \\ \vec{0} & \vec{p}^t & \vec{0} & \cdots & \vec{0} \\ \vdots & \vec{0} & \ddots & \ddots & \vdots \\ \vdots & \vdots & \ddots & \vec{p}^t & \vec{0} \\ \vec{0} & \cdots & \cdots & \vec{0} & \vec{p}^t \end{bmatrix} \begin{bmatrix} \vec{e}_1 \\ \vec{e}_2 \\ \vdots \\ \vec{e}_N \end{bmatrix} = P\vec{e} = \vec{I} \qquad (2)$$

where "P" is shorthand notation for the left-most bracketed quantity; "$\vec{e}$" is shorthand notation for the right-most bracketed quantity; "N" is the number of pixels of sensor system 110; and "$\vec{I}$" is the values of pixels 130 in image 132. In this example, "$\vec{0}$" in system of equations 208 is a zero vector with the same dimensionality as vector $\vec{p}^t$. Further, "t" in system of equations 208 is the transpose operator from linear algebra.

As depicted, equation generator 204 derives system of equations 208 from approximations for the $j^{th}$ pixel in pixels 130 of image 132 which is approximated as:

$$\vec{p} \begin{bmatrix} e^{-\mu(\varepsilon_1)x_j} \\ e^{-\mu(\varepsilon_2)x_j} \\ \vdots \\ e^{-\mu(\varepsilon_N)x_j} \end{bmatrix} = \vec{p}^t \vec{e}_{j=I_j} \quad (3)$$

where vector $e_j$ is shorthand notation for the column vector on the left hand side of the equation. In this illustrative example, j is an index for a pixel in an image.

In this illustrative example, equation solver 206 solves system of equations 208 by identifying a least squares solution for $\vec{e}$. Using a least squares solution is a least squares method. For example, equation solver 206 may convert system of equations 208 to:

$$\vec{e} = P^+ \vec{I} \quad (4)$$

where $P^+$ is a least squares operator. As depicted, equation solver 206 takes a component-wise natural-log of both sides of the equation to get:

$$\begin{bmatrix} \vec{\mu}x_1 \\ \vec{\mu}x_2 \\ \vdots \\ \vec{\mu}x_N \end{bmatrix} = \log(P^+ \vec{I}) \quad (5)$$

where $x_j$ are pixels of an object in pixels 130 in image 132. In this illustrative example, the pixels of the object are points in image 132 where ray-paths of energy from source 108 to sensor system 110 intersect with the object. In this illustrative example, equation solver 206 solves for the left hand side of the equation to identify "N" estimations of $\mu$ for $x_j$ after performing a component-wise division of each "$x_j$." Each identified value for each $\vec{\mu}x_j$ is an approximation of attenuation of energy for the object in image 132 at each "$x_j$." As depicted, equation solver 206 generates estimated attenuations 218 from the N estimations for $\vec{\mu}x_j$.

Figure 3:
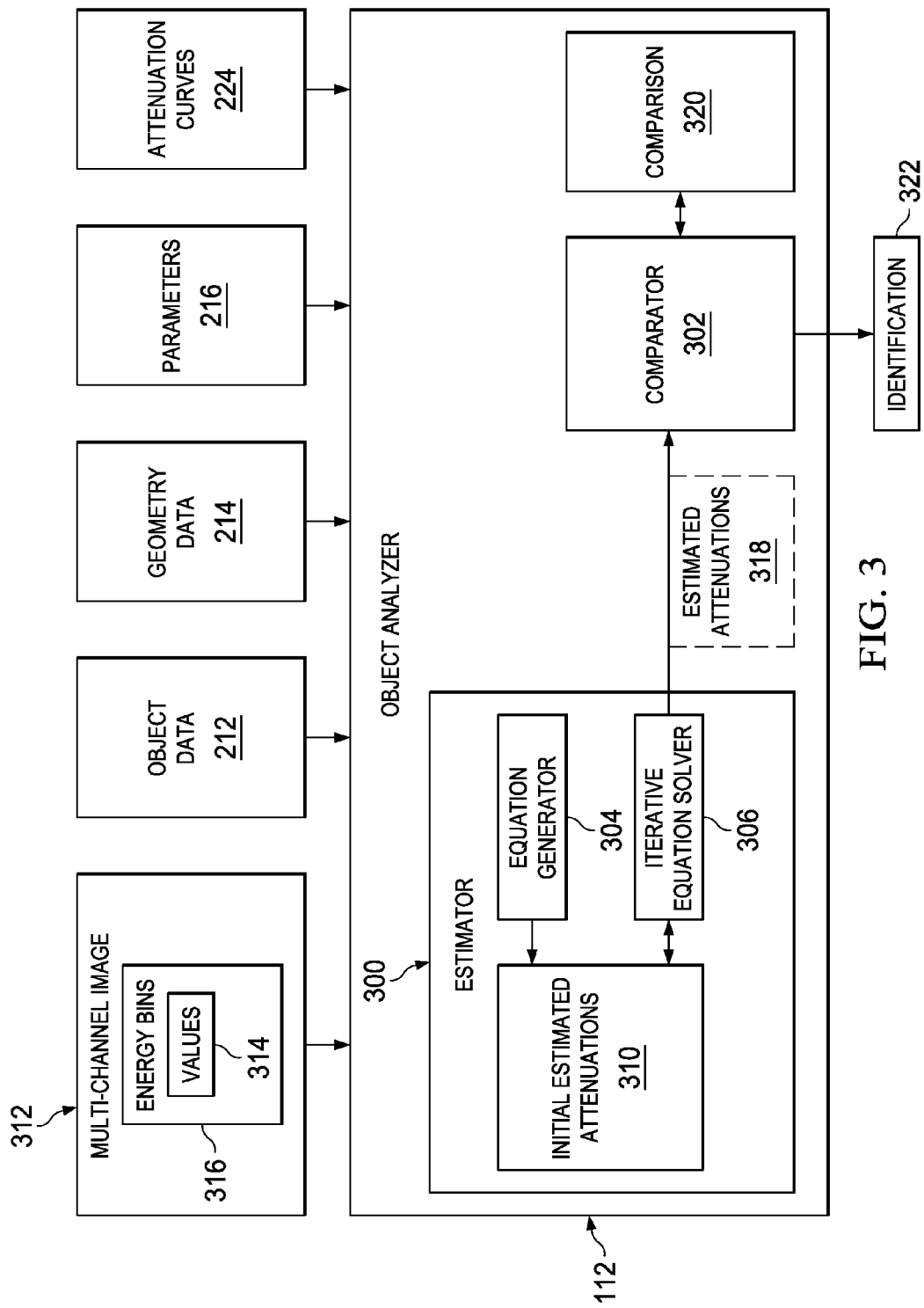
FIG. 3 is an illustration of a block diagram of an information flow for identifying material in an object in accordance with an illustrative embodiment.

With reference now to FIG. 3, an illustration of a block diagram of an information flow for identifying a material in an object is depicted in accordance with an illustrative embodiment. The information flow depicted in FIG. 3 is implemented by object analyzer 112.

In this illustrative example, object analyzer 112 includes estimator 300 and comparator 302. As depicted, estimator 300 includes equation generator 304 and iterative equation solver 306. In this illustrative example, equation generator 304 generates initial estimated attenuations 310.

In this example, iterative equation solver 306 uses initial estimated attenuations 310 as values for variables for a system of equations to identify attenuation of energy through points on an object. In this illustrative example, the object is located in multi-channel image 312.

In this illustrative example, equation generator 304 uses values 314 in energy bins 316 in multi-channel image 312 to generate initial estimated attenuations 310. As depicted, energy bins 316 are groups of pixels, and values 314 for energy bins 316 are amounts of energy 116 detected by pixels 128 in sensor system 110.

In this illustrative example, sensor system 110 is a multi-channel sensor. Each energy bin in energy bins 316 is a group of pixels in multi-channel image 312. Each energy bin in energy bins 316 is for a portion of values 314 for a range of energy levels detected by pixels 128 in sensor system 110. For example, each energy bin in energy bins 316 may be identified separately as a particular image in multi-channel image 312. As depicted, equation generator 304 also uses object data 212, geometry data 214, and parameters 216 to generate initial estimated attenuations 310.

Iterative equation solver 306 modifies initial estimated attenuations 310 for each energy bin in energy bins 316. Iterative equation solver 306 identifies initial estimated attenuations 310 as estimated attenuations 318 after modifying initial estimated attenuations 310 for each energy bin in energy bins 316. For example, iterative equation solver 306 may identify a group of energy bins in energy bins 316 that have not been processed by iterative equation solver 306. In this example, the group of energy bins are additional groups of pixels for an additional group of images in multi-channel image 312. Iterative equation solver 306 uses the additional group of images to generate an additional group of attenuations. The group of images may be referred to as an additional group of additional images. The additional group of attenuations may be referred to as additional estimated attenuations, or group of additional estimated attenuations. Iterative equation solver 306 modifies initial estimated attenuations 310 using the additional estimated attenuations. In this illustrative example, estimated attenuations 138 in FIG. 1 takes the form of estimated attenuations 318.

As depicted, comparator 302 receives estimated attenuations 318 for multi-channel image 312 from iterative equation solver 306. Comparator 302 generates comparison 320 by comparing estimated attenuations 318 to attenuation curves 224 for known materials. For example, comparator 302 may generate a curve from estimated attenuations 318. In this example, comparator 302 may then generate comparison 320 by comparing the curve generated by comparator 302 to attenuation curves 224 for known materials. The group of attenuation curves 224 for known materials is an example of known attenuation information 142 in FIG. 1.

In this illustrative example, comparison 320 is based on how well estimated attenuations 318 match the group of attenuation curves 224. Comparator 302 generates identification 322 based on comparison 320.

As depicted, identification 322 is an identification of material 104 in object 106 as identified from multi-channel image 312 of object 106. The identification may identify the material as a particular material. For example, the identification may be that the material is plastic, metal, titanium, aluminum, or some other type of material. The identification also may be that the material is unknown.

Equation generator 304 uses the following equation to model energy 116 being emitted from source 108 adjusted for attenuation through air:

$$I_O(\varepsilon)|_{\vec{z}} \approx \vec{p} \in \mathbb{R}^m, \varepsilon \in \mathbb{R} \quad (6)$$

where each component $p_i$ in $\vec{p}$ is approximately equal to $I_O(\epsilon)$; "$\epsilon$" is epsilon, and epsilon is the energy value of an x-ray photon; "$I_0(\epsilon)$" is a number of initial photons at epsilon; and "$\varepsilon_i$" in "$|_\varepsilon^i$" is a point within the domain of E and satisfies the following ordering:

$$\varepsilon_i - 1 < \varepsilon_i < \varepsilon_i + 1 \tag{7}$$

where $\mathbb{R}$ is the set of real numbers and "$\mathbb{R}^m$" is the set of real numbers in "m" dimensions of a coordinate system.

Equation generator 304 approximates the $j^{th}$ pixel of the object in multi-channel image 312 as:

$$\vec{p}_j^t \begin{bmatrix} e^{-\mu(\varepsilon_1)x_j} \\ e^{-\mu(\varepsilon_2)x_j} \\ \vdots \\ e^{-\mu(\varepsilon_N)x_j} \end{bmatrix} = \vec{p}_j^t \vec{e}_j = I_j \tag{8}$$

where $x_1$ is the length of the $j^{th}$ ray path from source 108 to the $j^{th}$ pixel in sensor system 110 that intersects with the object in multi-channel image 312; "e" is an exponential value; "$\mu(\epsilon)$" is attenuation with respect to epsilon; and vector $e_j$ is shorthand notation for the column vector on the left hand side of the equation. In this illustrative example, j is an index for a pixel in an image. "$I_j$" is a number of photons transmitted to pixel j of sensor system 110. In the illustrative example, each $\vec{p}_j$ varies to account for attenuation through air, the path length of energy 116 to each pixel in sensor system 110, and the path length through the object. In the depicted example, the lengths of the $j^{th}$ ray paths from source 108 to the $j^{th}$ pixel in sensor system 110 that intersect with the object in multi-channel image 312 are lengths of paths of energy 116 passing through the object to pixels in sensor system 110.

Equation generator 304 generates initial estimated attenuations 308 based on a system equations that takes the form of:

$$\begin{bmatrix} \vec{p}^t & \vec{0} & \cdots & \cdots & \vec{0} \\ \vec{0} & \vec{p}^t & \vec{0} & \cdots & \vec{0} \\ \vdots & \vec{0} & \ddots & \ddots & \vdots \\ \vdots & \vdots & \ddots & \vec{p}^t & \vec{0} \\ \vec{0} & \cdots & \cdots & \vec{0} & \vec{p}^t \end{bmatrix} \begin{bmatrix} \vec{e}_1 \\ \vec{e}_2 \\ \vdots \\ \vec{e}_N \end{bmatrix} = P\vec{e} = \vec{I} \tag{9}$$

where "P" is a shorthand notation for the left-most bracketed quantity; "$\vec{e}$" is shorthand notation for the right-most bracketed quantity, "N" is the number of pixels of sensor system 110; "$\vec{I}$" is the values of pixels 130 in image 132; "$\vec{0}$" in the system of equations is a zero vector with the same dimensionality as vector $\vec{p}^t$; and "t" in the system of equations is the transpose operator from linear algebra.

In this illustrative example, iterative equation solver 306 uses a direct search method to identify estimated attenuations 318. A direct search method is an optimization technique for identifying a solution to a system of equations. The direct search method is an iterative method. The direct search method identifies the solution to the system of equations by iteratively improving on an initial solution to the system of equations.

In this illustrative example, the direct search method used is the Nelder-Mead direct search method. Iterative equation solver 306 uses the direct search method to estimate attenuations for each energy bin in energy bins 316 as the sum of the first five Legendre Polynomials using the following equation:

$$\vec{\hat{\mu}}(\varepsilon) = \Sigma_{i=0}^{4} c_i p_i(\varepsilon) \tag{10}$$

where $\hat{\mu}(\varepsilon)$ is estimated attenuations of epsilon; $c_i$ for i ∈ [0, 1, 2, 3, 4] are values for variables being optimized with respect to the objective function of the system of equations; $p_i(\varepsilon)$ is the $i^{th}$ Legendre Polynomial; and the domain for each energy bin in energy bins 316 is scaled to the interval [−1, 1]. The domain for the each energy bin is scaled to the interval [−1, 1] to preserve orthogonality between the energy bins.

The illustration of material identification environment 100 in the different components in material identification environment 100 in FIGS. 1-3 are not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, information 124 may include other information in addition to or in place of images 126. For example, sensor system 110 may generate information 124 about object 106, such as dimensions, orientation, or other suitable information.

In yet another illustrative example, equation generator 204 and equation solver 206 may be implemented as a single component. In still another illustrative example, object analyzer 112 in FIG. 2 and FIG. 3 may include other components in addition to or in place of the ones depicted. For example, object analyzer 112 may include an action identifier in FIG. 2 and FIG. 3. The action identifier may use identification 226 and identification 322 to identify or select an action to be taken with respect to object 106.

Figure 4:
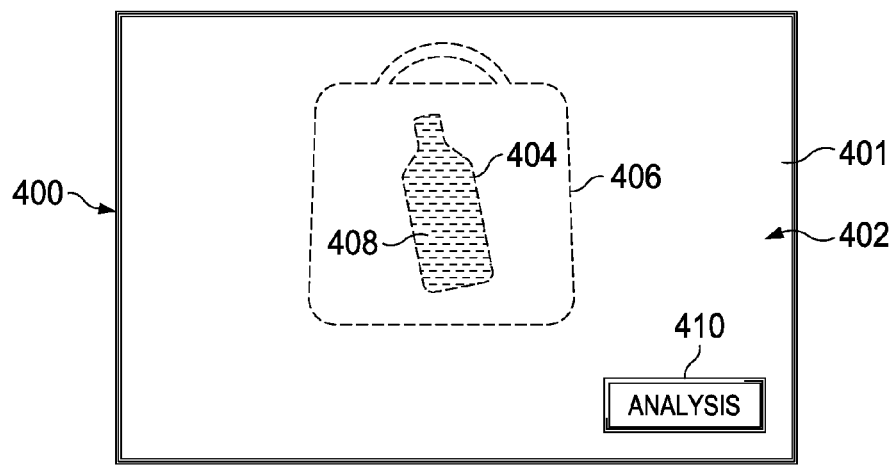
FIG. 4 is an illustration of a graphical user interface with an x-ray image in accordance with an illustrative embodiment.

FIGS. 4-8 are illustrative examples of a graphical user interface that may be used to interact with an object analyzer to identify material in an object from an x-ray image. With reference first to FIG. 4, an illustration of a graphical user interface with an x-ray image is depicted in accordance with an illustrative embodiment. Graphical user interface 400 is an example of one implementation for graphical user interface 146 shown in block form in FIG. 1.

As depicted, graphical user interface 400 displays pixels 401 for x-ray image 402. X-ray image 402 is an example of image 132 shown in block form in FIG. 1, and pixels 401 are examples of pixels 130 shown in block form in FIG. 1.

In the illustrative example, x-ray image 402 includes water bottle 404, bag 406, and material 408 in water bottle 404. Analysis button 410 is for identifying material 408 in water bottle 404 in x-ray image 402. As depicted, selection of analysis button 410 sends a request to an object analyzer to identify material 408 in water bottle 404 in x-ray image 402.

Figure 5:
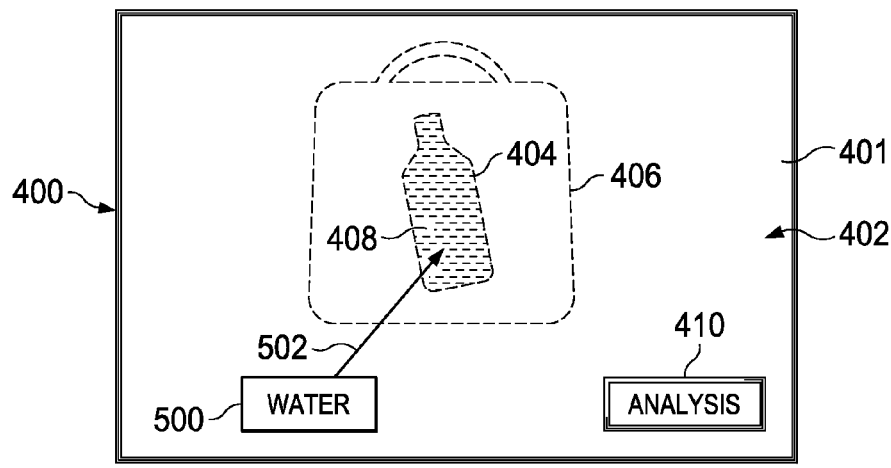
FIG. 5 is an illustration of a graphical user interface displaying information about a material in an object in accordance with an illustrative embodiment.

Turning next to FIG. 5, an illustration of a graphical user interface displaying information about a material in an object is depicted in accordance with an illustrative embodiment. In this illustrative example, analysis button 410 has been pressed.

As depicted, graphical user interface 400 displays indicator 500. Indicator 500 is a text box that identifies material 408 as water. Arrow 502 in graphical user interface 400 visually indicates where the water is located.

Figure 6:
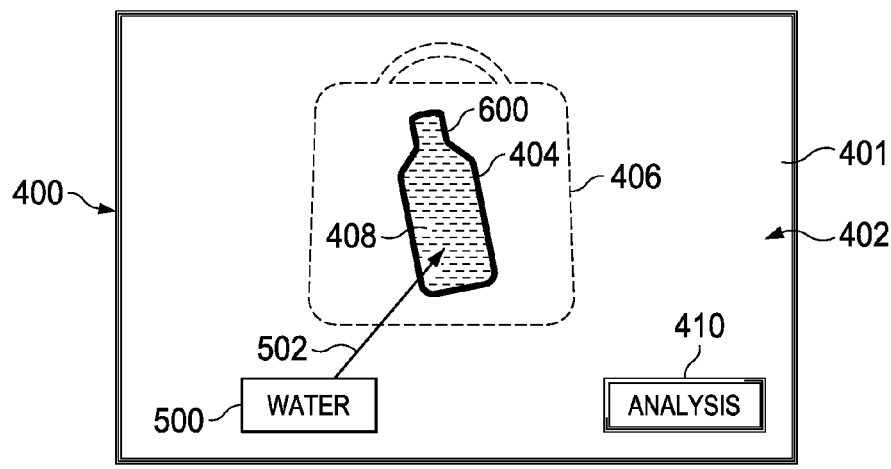
FIG. 6 is an illustration of a graphical user interface displaying information about a material in an object in accordance with an illustrative embodiment.

Referring now to FIG. 6, an illustration of a graphical user interface displaying information about a material in an object is depicted in accordance with an illustrative embodiment. In this illustrative example, graphical user interface 400 displays outline indicator 600. Outline indicator 600 is an outline of material 408 in water bottle 404 that highlights where the water is located.

In this illustrative example, outline indicator 600 is a bright white outline. Outline indicator 600 may be any suitable color. For example, when material 408 is a banned substance, outline indicator 600 may be red to indicate material 408 is banned.

The illustration of graphical user interface 400 in FIGS. 4-6 are not meant to limit the manner in which graphical user interface 146 shown in block form in FIG. 1 may be displayed in display system 148. For example, graphical user interface 146 may include instructions for how to handle material in an object in an x-ray image. As another example, graphical user interface 146 may receive user input identifying an object from a plurality of objects in an x-ray image to identify material for.

As still another example, graphical user interface 146 may receive user input identifying a sub-object of an object to omit from an analysis of the material in the object.

Figure 7:
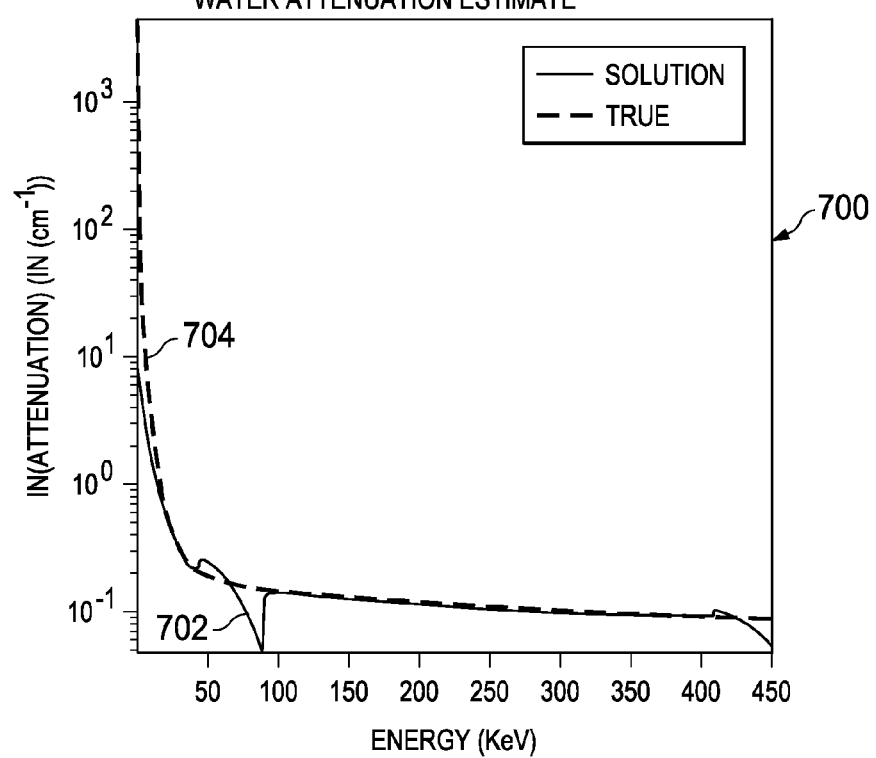
FIG. 7 is an illustration of a graphical user interface displaying information about a material in an object in accordance with an illustrative embodiment.

Referring next to FIG. 7, an illustration of a graphical user interface displaying information about a material in an object is depicted in accordance with an illustrative embodiment. In this illustrative example, graphical user interface 400 displays graph 700.

As depicted, graph 700 includes estimated attenuations 702 for material 408 in water bottle 404 and attenuation curve 704 for water. Graph 700 enables a visual comparison to be made by a human operator as to how close estimated attenuations 702 for material 408 in water bottle 404 are to attenuation curve 704 for water.

Figure 8:
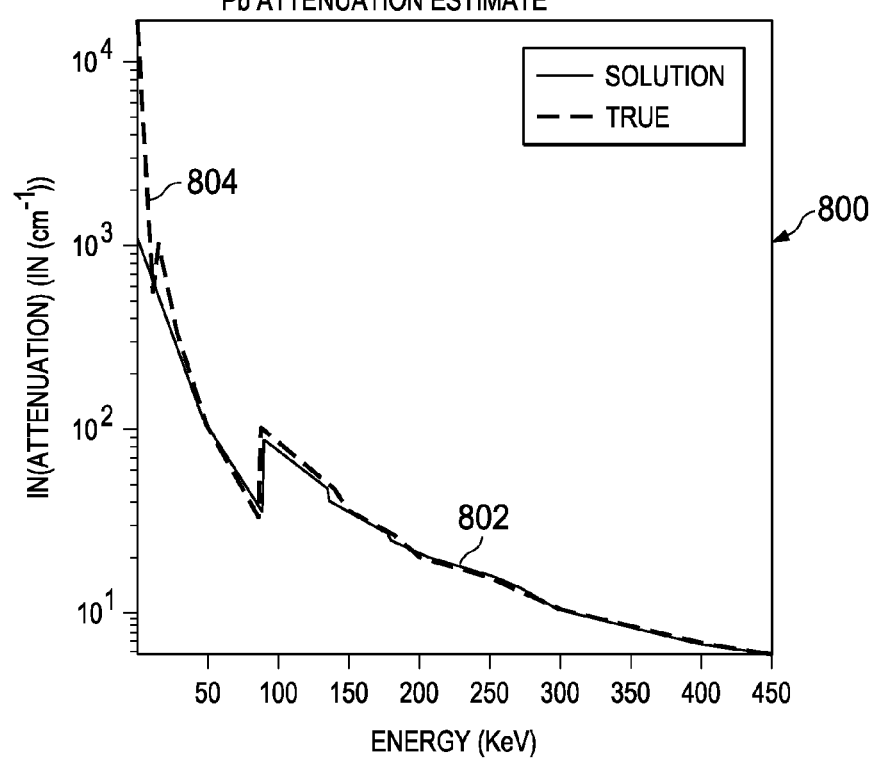
FIG. 8 is an illustration of a graphical user interface displaying information about a material in an object in accordance with an illustrative embodiment.

Referring next to FIG. 8, an illustration of a graphical user interface displaying information about a material in an object is depicted in accordance with an illustrative embodiment. In this illustrative example, graphical user interface 400 displays graph 800.

As depicted, graph 800 includes estimated attenuations 802 for a material in an object in an x-ray image. Graph 800 also includes attenuation curve 804 for lead. Displaying graph 800 enables a visual comparison of how close estimated attenuations 802 for the material in the object in the x-ray image are to attenuation curve 804 for lead.

Figure 9:
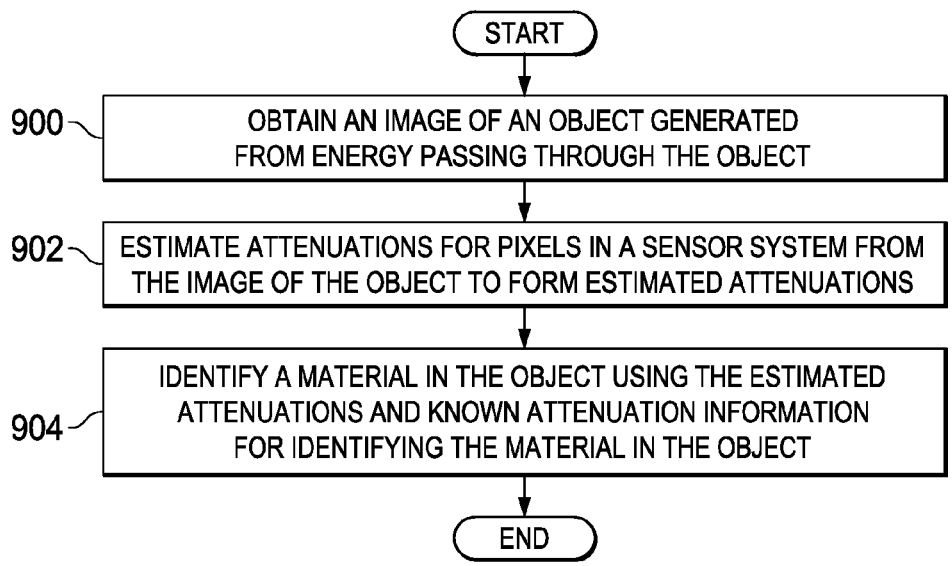
FIG. 9 is an illustration of a flowchart of a process for identifying a material in an object in accordance with an illustrative embodiment.

Turning next to FIG. 9, an illustration of a flowchart of a process for identifying a material in an object is depicted in accordance with an illustrative embodiment. The process illustrated in FIG. 9 may be implemented in material identification environment 100 in FIG. 1. In particular, the different steps in this flowchart may be implemented in object analyzer 112 to identify material 104 in object 106 in FIG. 1.

The process begins by obtaining an image of an object generated from energy passing through the object (step 900). The process then estimates attenuations for pixels in a sensor system from the image of the object to form estimated attenuations (step 902). The estimated attenuations represent a loss of the energy that occurs from the energy passing through the object.

The process identifies a material in the object using the estimated attenuations and known attenuation information for identifying the material in the object (step 904), with the process terminating thereafter.

The result of the steps in FIG. 9 may be displayed as a result on a graphical user interface on a display system. The display of the results may be used by an operator to identify actions that may be performed with respect to the object based on the identification of the material in the object.

Figure 10:
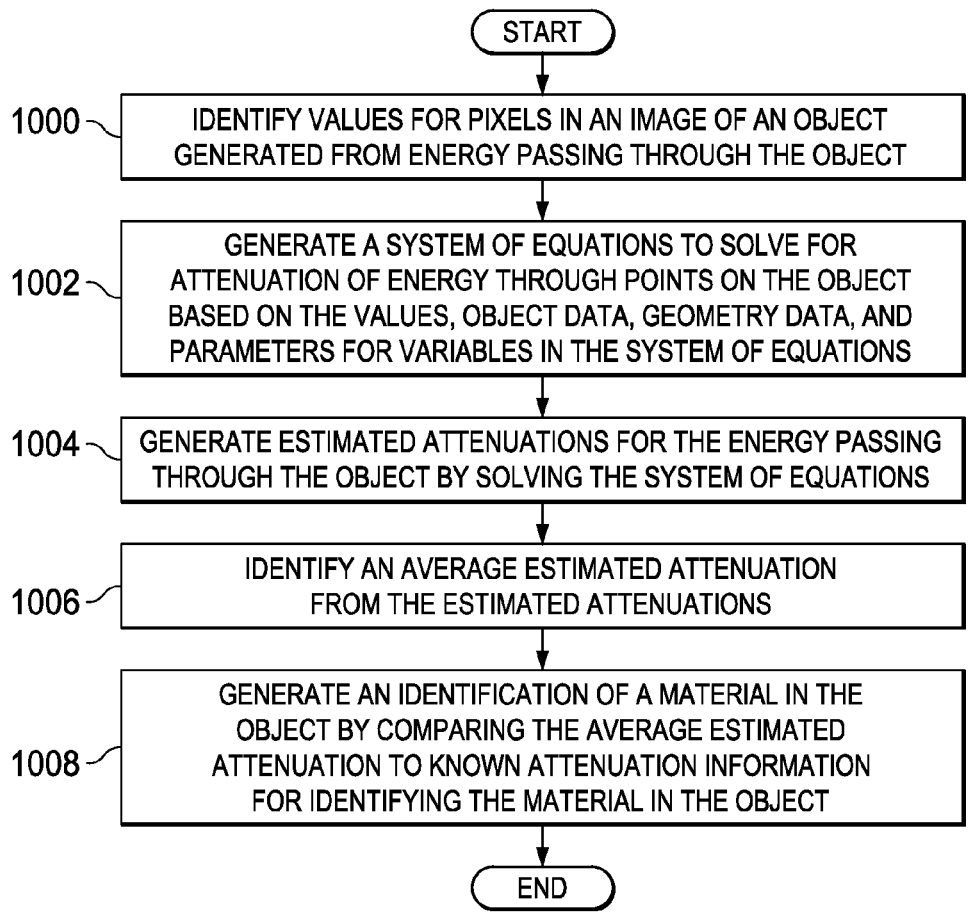
FIG. 10 is an illustration of a flowchart of a process for identifying a material in an object in accordance with an illustrative embodiment.

With reference next to FIG. 10, an illustration of a flowchart of a process for identifying a material in an object is depicted in accordance with an illustrative embodiment. The process illustrated in FIG. 10 may be implemented in material identification environment 100 in FIG. 1. In particular, the different steps in this flowchart may be implemented in object analyzer 112 in FIG. 2 to generate identification 226 in FIG. 2.

The process begins by identifying values for pixels in an image of an object generated from energy passing through the object (step 1000). The process generates a system of equations to solve for attenuation of energy through points on the object based on the values, object data, geometry data, and parameters for variables in the system of equations (step 1002).

The process next generates estimated attenuations for the energy passing through the object by solving the system of equations (step 1004). The process identifies an average estimated attenuation from the estimated attenuations (step 1006). The process then generates an identification of a material in the object by comparing the average estimated attenuation to known attenuation information for identifying the material in the object (step 1008), with the process terminating thereafter.

Figure 11:
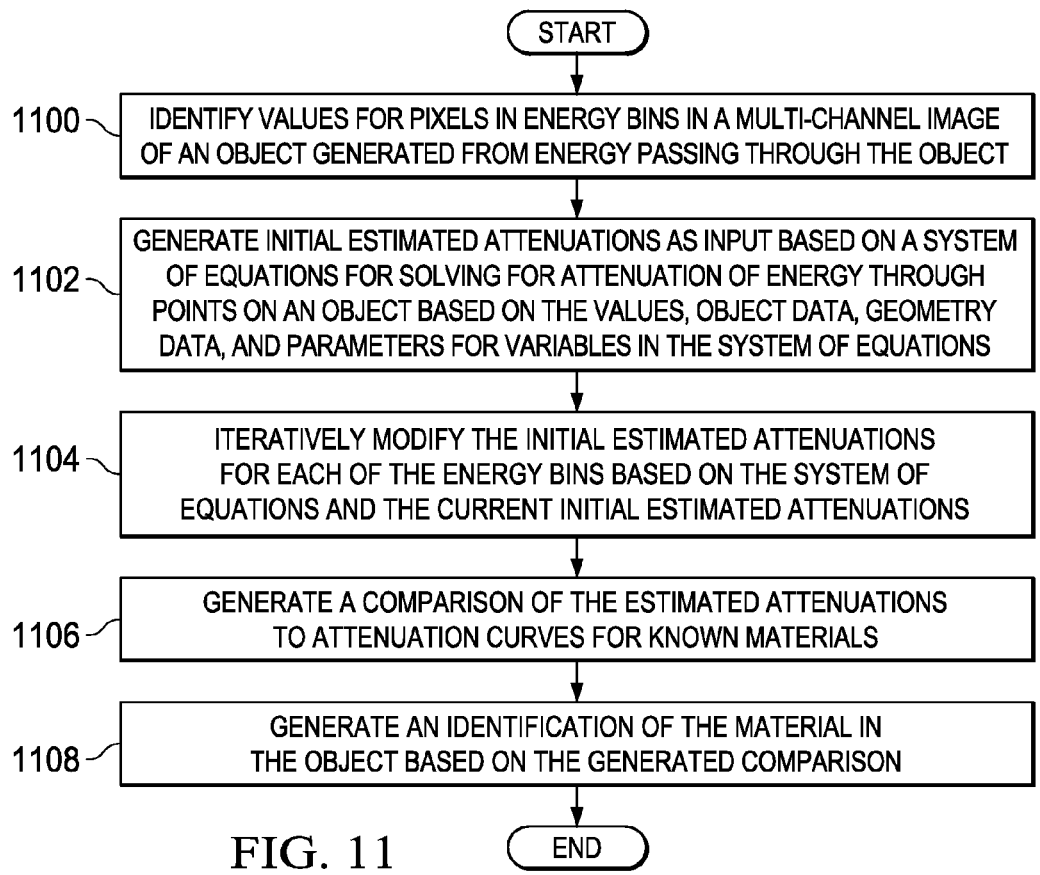
FIG. 11 is an illustration of a flowchart of a process for identifying a material in an object in accordance with an illustrative embodiment.

With reference next to FIG. 11, an illustration of a flowchart of a process for identifying a material in an object is depicted in accordance with an illustrative embodiment. The process illustrated in FIG. 11 may be implemented in material identification environment 100 in FIG. 1. In particular, the different steps in this flowchart may be implemented in object analyzer 112 in FIG. 3 to generate identification 322 in FIG. 3.

The process begins by identifying values for pixels in energy bins in a multi-channel image of an object generated from energy passing through the object (step 1100). The process then generates initial estimated attenuations as input based on a system of equations for solving for attenuation of energy through points on an object based on the values, object data, geometry data, and parameters for variables in the system of equations (step 1102). The process iteratively modifies the initial estimated attenuations for each of the energy bins based on the system of equations and the current initial estimated attenuations (step 1104). The process generates a comparison of the estimated attenuations to attenuation curves for known materials (step 1106). The process then generates an identification of the material in the object based on the generated comparison (step 1108), with the process terminating thereafter.

Figure 12:
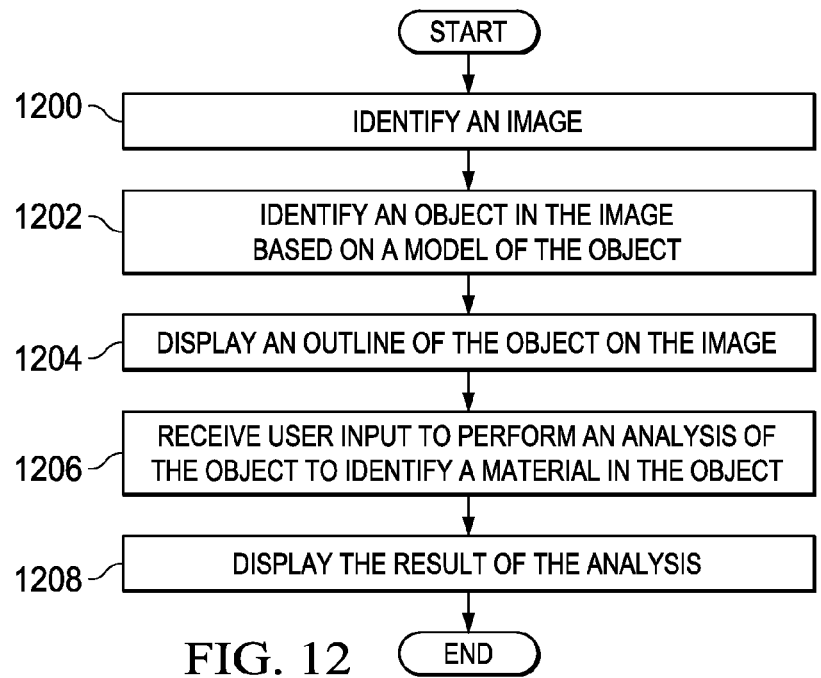
FIG. 12 is an illustration of a flowchart of a process for identifying a material in an object in accordance with an illustrative embodiment.

With reference next to FIG. 12, an illustration of a flowchart of a process for identifying a material in an object is depicted in accordance with an illustrative embodiment. The process illustrated in FIG. 12 may be implemented in material identification environment 100 in FIG. 1. In particular, the different steps in this flowchart may be implemented using object scanning system 102 in FIG. 1.

The process begins by identifying an image (step 1200). The process identifies an object in the image based on a model of the object (step 1202). The process displays an outline of the object on the image (step 1204). The process receives user input to perform an analysis of the object to identify a material in the object (step 1206). The process displays the result of the analysis (step 1208), with the process terminating thereafter. In this illustrative example, the result in step 1208 includes an identification of the material in the object. The result may also include other information. For example, information may include an action to be taken, an identification of the object itself, or other suitable information.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent at least one of a module, a segment, a function, or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams. When implemented as a combination of program code and hardware, the implementation may take the form of firmware.

In some alternative implementations of an illustrative embodiment, the function or functions noted in the blocks may occur out of the order noted in the figures. For example, in some cases, two blocks shown in succession may be performed substantially concurrently, or the blocks may sometimes be performed in the reverse order, depending upon the functionality involved. Also, other blocks may be added in addition to the illustrated blocks in a flowchart or block diagram.

Figure 13:
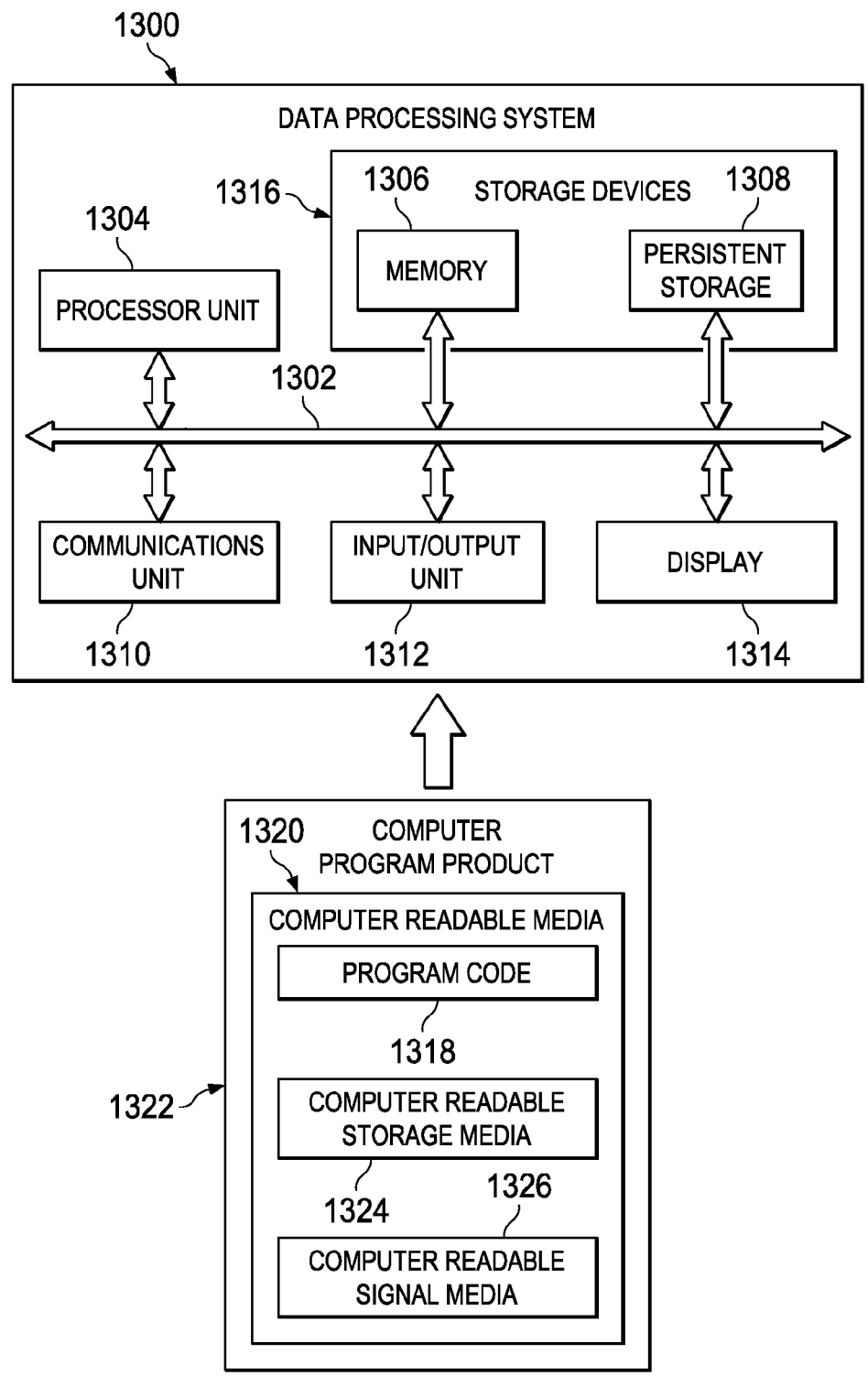
FIG. 13 is an illustration of a block diagram of a data processing system in accordance with an illustrative embodiment.

Turning now to FIG. 13, an illustration of a block diagram of a data processing system is depicted in accordance with an illustrative embodiment. Data processing system 1300 may be used to implement computer system 134 in FIG. 1. In this illustrative example, data processing system 1300 includes communications framework 1302, which provides communications between processor unit 1304, memory 1306, persistent storage 1308, communications unit 1310, input/output (I/O) unit 1312, and display 1314. In this example, communication framework may take the form of a bus system.

Processor unit 1304 serves to execute instructions for software that may be loaded into memory 1306. Processor unit 1304 may be a number of processors, a multi-processor core, or some other type of processor, depending on the particular implementation.

Memory 1306 and persistent storage 1308 are examples of storage devices 1316. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 1316 may also be referred to as computer readable storage devices in these illustrative examples. Memory 1306, in these examples, may be, for example, a random access memory or any other suitable volatile or non-volatile storage device. Persistent storage 1308 may take various forms, depending on the particular implementation.

For example, persistent storage 1308 may contain one or more components or devices. For example, persistent storage 1308 may be a hard drive, a flash memory, a rewritable optical disk, a rewritable magnetic tape, or some combination of the above. The media used by persistent storage 1308 also may be removable. For example, a removable hard drive may be used for persistent storage 1308.

Communications unit 1310, in these illustrative examples, provides for communications with other data processing systems or devices. In these illustrative examples, communications unit 1310 is a network interface card.

Input/output unit 1312 allows for input and output of data with other devices that may be connected to data processing system 1300. For example, input/output unit 1312 may provide a connection for user input through at least of a keyboard, a mouse, or some other suitable input device. Further, input/output unit 1312 may send output to a printer. Display 1314 provides a mechanism to display information to a user.

Instructions for at least one of the operating system, applications, or programs may be located in storage devices 1316, which are in communication with processor unit 1304 through communications framework 1302. The processes of the different embodiments may be performed by processor unit 1304 using computer-implemented instructions, which may be located in a memory, such as memory 1306.

These instructions are referred to as program code, computer usable program code, or computer readable program code that may be read and executed by a processor in processor unit 1304. The program code in the different embodiments may be embodied on different physical or computer readable storage media, such as memory 1306 or persistent storage 1308.

Program code 1318 is located in a functional form on computer readable media 1320 that is selectively removable and may be loaded onto or transferred to data processing system 1300 for execution by processor unit 1304. Program code 1318 and computer readable media 1320 form computer program product 1322 in these illustrative examples. In one example, computer readable media 1320 may be computer readable storage media 1324 or computer readable signal media 1326.

In these illustrative examples, computer readable storage media 1324 is a physical or tangible storage device used to store program code 1318 rather than a medium that propagates or transmits program code 1318.

Alternatively, program code 1318 may be transferred to data processing system 1300 using computer readable signal media 1326. Computer readable signal media 1326 may be, for example, a propagated data signal containing program code 1318. For example, computer readable signal media 1326 may be at least one of an electromagnetic signal, an optical signal, or any other suitable type of signal. These signals may be transmitted over at least one of communications links, such as wireless communications links, optical fiber cable, coaxial cable, a wire, or any other suitable type of communications link.

The different components illustrated for data processing system 1300 are not meant to provide architectural limitations to the manner in which different embodiments may be implemented. The different illustrative embodiments may be implemented in a data processing system including components in addition to or in place of those illustrated for data processing system 1300. Other components shown in FIG. 13 can be varied from the illustrative examples shown. The different embodiments may be implemented using any hardware device or system capable of running program code 1318.

Thus, the illustrative embodiments provide a method and apparatus for analyzing objects. For example, the illustrative embodiments may be implemented to identify materials in objects. These embodiments may identify materials in objects more quickly and with a greater specificity than currently available object scanning systems. In the illustrative examples, attenuations are estimated for x-rays passing through an object. These estimated attenuations are compared to attenuations for known materials. The comparison is used to identify the material.

As a result, the identification and other information may be displayed, or otherwise presented, to an operator. The operator may then take appropriate actions with respect to the object. For example, in a manufacturing environment, the operator may determine whether to repair the object, rework the object, discard the object, or pass the object on for further manufacturing operations or for delivery to the client. In a baggage scanning environment, the operator may flag the object for further inspection, allow the object to pass on, confiscate the object, or perform some other suitable action.

The description of the different illustrative embodiments has been presented for purposes of illustration and description and is not intended to be exhaustive or limited to the embodiments in the form disclosed. The different illustrative examples describe components that perform actions or operations. In an illustrative embodiment, a component may be configured to perform the action or operation described. For example, the component may have a configuration or design for a structure that provides the component an ability to perform the action or operation that is described in the illustrative examples as being performed by the component.

Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An object identification system comprising:
   a single X-ray source, the single X-ray source configured to produce mono-energetic X-rays;
   a detector configured to detect X-rays from the single X-ray source that pass through an object;
   an object analyzer in communication with the detector and the single X-ray source, the object analyzer:
      obtains an image of an object generated from the mono-energetic X-rays passing through the object;
      estimates attenuations for pixels in a sensor system from the image of the object to form estimated attenuations, wherein the attenuations represent a loss of energy that occurs from the mono-energetic X-rays passing through the object; and
      identifies a material in the object using the estimated attenuations and known attenuation information for identifying the material in the object.

2. The object identification system of claim 1, wherein in estimating the attenuations for the pixels in the sensor system from the image of the object to form the estimated attenuations, the object analyzer:
   identifies values of the mono-energetic X-rays detected by the pixels in the sensor system; and
   solves a system of equations to identify the estimated attenuations based on the values of the mono-energetic X-rays detected by the pixels.

3. The object identification system of claim 1, wherein in identifying the material in the object using the estimated attenuations and the known attenuation information for identifying the material in the object, the object analyzer:
   generates an average estimated attenuation for the object in the image from the estimated attenuations;
   compares the average estimated attenuation to a group of attenuation curves for known materials to form a comparison; and
   generates an identification of the material from the comparison.

4. The object identification system of claim 1, wherein the mono-energetic X-rays have a profile and wherein in estimating the attenuations for the pixels in the sensor system from the image of the object to form the estimated attenuations, the object analyzer identifies energy loss that occurs from amounts of X-ray energy passing through the object.

5. The object identification system of claim 1, wherein in estimating the attenuations for the pixels in the sensor system from the image of the object to form the estimated attenuations, the object analyzer:
   identifies lengths of paths of the mono-energetic X-rays passing through the object to the pixels in the sensor system;
   identifies values of the mono-energetic X-rays detected by the pixels in the sensor system; and
   solves a system of equations to identify the estimated attenuations based on the values of the mono-energetic X-rays detected by the pixels and the lengths of the paths of the mono-energetic X-rays passing through the object.

6. The object identification system of claim 1, wherein in estimating the attenuations for the pixels in the sensor system from the image of the object to form the estimated attenuations, the object analyzer uses a direct search method, wherein the direct search method comprises an iterative optimization technique for identifying a solution to a system of equations.

7. The object identification system of claim 2, wherein the object analyzer generates the system of equations based on the pixels in the sensor system and information about the single X-ray source.

8. The object identification system of claim 7, wherein the system of equations is selected from one of a system of linear equations, a system of non-linear equations, a pseudo-inverse, and a matrix inversion.

9. The object identification system of claim 7, wherein the system of equations is solved by the object analyzer using at least one of a least squares method or an iterative method.

10. An object identification system comprising:
   an object analyzer that:
      obtains an image of an object generated from energy passing through the object;
      estimates attenuations for pixels in a sensor system from the image of the object to form estimated attenuations, wherein the attenuations represent a loss of energy that occurs from the energy passing through the object; and
      identifies a material in the object using the estimated attenuations and known attenuation information for identifying the material in the object;
   wherein in estimating the attenuations for the pixels in the sensor system from the image of the object to form the estimated attenuations, the object analyzer:
      estimates the attenuations for the pixels from the image and an additional group of attenuations for the pixels in the sensor system from an additional group of images of the object to form the estimated attenuations and additional estimated attenuations and wherein in identifying the material in the object using the estimated attenuations and the known attenuation information for identifying the material in the object, the object analyzer:
generates average estimated attenuations for the object from the image and a group of additional estimated attenuations from an additional group of additional images for the object;
forms a curve from the average estimated attenuations;
compares the curve to a group of attenuation curves in the known attenuation information for identifying the material in the object to form a comparison; and
generates an identification of the material from the comparison.

11. The object identification system of claim 10, wherein in comparing the curve to the group of attenuation curves in the known attenuation information for identifying the material in the object to form the comparison, the object analyzer searches the group of attenuation curves for types of materials for a closest match to the estimated attenuations using a discrete search method to form the comparison.

* * * * *